(12) United States Patent
Hidaka et al.

(10) Patent No.: US 11,020,685 B2
(45) Date of Patent: Jun. 1, 2021

(54) METHOD FOR PRODUCING ALCOHOL

(71) Applicant: Mitsubishi Chemical Corporation, Chiyoda-ku (JP)

(72) Inventors: Hideto Hidaka, Chiyoda-ku (JP); Yohei Sato, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/570,117

(22) Filed: Sep. 13, 2019

(65) Prior Publication Data

US 2020/0001199 A1 Jan. 2, 2020

Related U.S. Application Data

(63) Continuation of application No. PCT/JP2018/009032, filed on Mar. 8, 2018.

(30) Foreign Application Priority Data

Mar. 14, 2017 (JP) .............................. JP2017-048628

(51) Int. Cl.
*B01D 3/14* (2006.01)
*C07C 29/80* (2006.01)
*C07C 31/08* (2006.01)

(52) U.S. Cl.
CPC .............. *B01D 3/146* (2013.01); *C07C 29/80* (2013.01); *C07C 31/08* (2013.01)

(58) Field of Classification Search
CPC .......... B01D 3/146; C07C 29/80; C07C 31/08
See application file for complete search history.

(56) References Cited

U.S. PATENT DOCUMENTS

| 5,131,928 A * | 7/1992 | Blackman | .............. | B01D 53/22 |
| | | | | 210/500.41 |
| 7,070,694 B2 * | 7/2006 | Colling | .................... | B01D 3/14 |
| | | | | 203/19 |

(Continued)

FOREIGN PATENT DOCUMENTS

| JP | 58-183634 A | 10/1983 |
| JP | 61-254177 A | 11/1986 |

(Continued)

OTHER PUBLICATIONS

International Search Report dated Apr. 10, 2018 in PCT/JP2018/009032, 1 page.

(Continued)

*Primary Examiner* — Jonathan Miller
(74) *Attorney, Agent, or Firm* — Oblon, McClelland, Maier & Neustadt, L.L.P.

(57) ABSTRACT

The object is to provide a method for producing an alcohol by applying a multiple-effect method to improve the energy efficiency of the whole process. The object is achieved by a method for producing an alcohol including a concentration step of introducing a water-alcohol mixed solution into a multiple-effect distillation column for concentrating the same; a condensation step of introducing a vapor recovered from the top of the distillation column into a condenser for condensing the same; and a separation step of introducing the water-alcohol mixed solution condensed in the condensation step in a liquid phase into a membrane separation apparatus for separating the water and alcohol in the mixed solution.

14 Claims, 3 Drawing Sheets

(56) References Cited

U.S. PATENT DOCUMENTS

| | | | | |
|---|---|---|---|---|
| 9,120,882 | B2* | 9/2015 | Janssens | C08F 110/06 |
| 9,266,803 | B2* | 2/2016 | Vane | B01D 61/36 |
| 10,683,246 | B2* | 6/2020 | Liu | B01D 3/007 |
| 2004/0182786 | A1* | 9/2004 | Colling | C07C 7/144 |
| | | | | 210/640 |
| 2008/0135396 | A1* | 6/2008 | Blum | B01D 3/148 |
| | | | | 203/25 |
| 2008/0167512 | A1* | 7/2008 | Sanders | C07C 7/144 |
| | | | | 585/818 |
| 2009/0057128 | A1* | 3/2009 | Vane | C07C 29/80 |
| | | | | 203/17 |
| 2009/0301970 | A1* | 12/2009 | Noel | B01D 3/002 |
| | | | | 210/640 |
| 2012/0137727 | A1* | 6/2012 | Huang | C07C 29/76 |
| | | | | 62/617 |
| 2015/0224420 | A1* | 8/2015 | Hickey | B01D 3/145 |
| | | | | 203/41 |
| 2016/0107964 | A1* | 4/2016 | Matsukata | C07C 31/08 |
| | | | | 568/913 |
| 2017/0203230 | A1* | 7/2017 | Raiser | B01D 3/007 |
| 2017/0204030 | A1* | 7/2017 | Maeda | B01D 71/028 |
| 2019/0100479 | A1* | 4/2019 | Liu | B01D 71/06 |
| 2019/0336882 | A1* | 11/2019 | Andrade | B01D 3/145 |
| 2019/0352244 | A1* | 11/2019 | Yamamura | C07C 31/08 |

FOREIGN PATENT DOCUMENTS

| | | |
|---|---|---|
| JP | 2002-155000 A | 5/2002 |
| JP | 2012-67091 A | 4/2012 |
| JP | 2016-41419 A | 3/2016 |

OTHER PUBLICATIONS

English translation of the International Preliminary Report on Patentability and Written Opinion of the International Searching Authority dated Sep. 26, 2019 in PCT/JP2018/009032 filed Mar. 8, 2018, 6 pages.

Kou Izumi, et al., "Energy Saving in Fuel Ethanol Concentrating and Dehydrating Process Using Zeolite Membrane" Chemical Engineering of Japan, vol. 71, No. 12, 2007, pp. 812-816 (with English translation).

"Standard Technology Collection—Water Treatment: 1-12-2-1 Multiple-Effect Method" Japan Patent Office, 2005, (with unedited computer generated English translation).

* cited by examiner

METHOD FOR PRODUCING ALCOHOL

CROSS-REFERENCE TO RELATED APPLICATION

This is a continuation of International Application No. PCT/JP2018/009032, filed on Mar. 8, 2018, and designated the U.S., and claims priority from Japanese Patent Application No. 2017-048628 which was filed on Mar. 14, 2017, the entire contents of which are incorporated herein by reference.

TECHNICAL FIELD

The present invention relates to a method for producing an alcohol, and especially to a method for producing an alcohol with improved energy efficiency using a multiple-effect distillation column.

BACKGROUND ART

In recovering an alcohol from a water-alcohol mixture, it is difficult to purify the organic compound to have a high purity solely by ordinary distillation, because the mixture of water and an alcohol forms an azeotropic mixture which has a minimum boiling point. Therefore, the water-alcohol mixture whose alcohol concentration has been enhanced by a distillation column is supplied to a PSA, a membrane separation apparatus, or the like to separate water and alcohol to increase the alcohol concentration.

When a membrane dehydration method is used as a separation method, it is said that there is an advantage over a PSA method because it has still better energy saving property, and is able to treat a water-containing ethanol having an alcohol concentration lower than an ordinary water-containing ethanol (Non Patent Literature 1). As specific examples utilizing a membrane separation apparatus, a method in which a liquid recovered from the bottom or a middle stage of a distillation column is fed to a membrane separation apparatus, and a method in which a gas recovered from the top or a middle stage of a distillation column is fed to a membrane separation apparatus are described in Patent Literature 1.

Meanwhile, in the field of water treatment utilizing evaporation, the so-called multiple-effect method, in which the vapor generated by evaporation is used for other evaporation so as to improve the overall energy efficiency, has been known (Non Patent Literature 2).

PRIOR ART REFERENCES

Patent Literatures

[Patent Literature 1] Japanese Patent Laid-Open No. 2012-067091 Non Patent Literatures
[Non Patent Literature 1] CHEMICAL ENGINEERING OF JAPAN, Vol. 71 (12), 812 to 816 (2007)
[Non Patent Literature 2] Standard Technology Collection—Water Treatment: 1-12-2-1 Multiple-Effect Method, Japan Patent Office 2005

SUMMARY OF THE INVENTION

The present inventors attempted to apply a multiple-effect method to the process of producing an alcohol from a water-alcohol mixture, and when a liquid recovered from the bottom or a middle stage of a distillation column was fed to a membrane separation apparatus, the liquid was required to be vaporized again for applying the multiple-effect method, which worsened the energy efficiency. Whereas when a gas recovered from the top or a middle stage of a distillation column was fed to a membrane separation apparatus, although the multiple-effect method could be applied after partial condensation of the gas, the amount of heat that could be utilized for other distillation was limited because of partial condensation, and an adequate effect of the multiple-effect method could not be obtained.

An object of the present invention is to provide a process in which the overall energy efficiency is improved by applying a multiple-effect method to a process for producing an alcohol from a water-alcohol mixture.

The inventors of the present invention conducted intensive studies for achieving the object to find that the object could be achieved by condensing the gas recovered from the top of a distillation column by a condenser, utilizing the heat of condensation developed at this time for the multiple-effect method, and feeding the condensed liquid to a membrane separation apparatus by a pervaporation method, thereby arriving at the invention.

That is, the outline of the present invention is as follows.
[1] A method for producing an alcohol comprising:
a concentration step of introducing a water-alcohol mixed solution into a multiple-effect distillation column to concentrate the water-alcohol mixed solution;
a condensation step of introducing a vapor recovered from the top of the multiple-effect distillation column into a condenser to condense the vapor; and
a separation step of introducing the water-alcohol mixed solution condensed in the condensation step in a liquid phase into a membrane separation apparatus to separate the water and alcohol in the mixed solution.
[2] The method for producing an alcohol according to [1] above, wherein the vapor recovered from the top of the multiple-effect distillation column is introduced into a condenser, and condensed totally in the condensation step.
[3] The method for producing an alcohol according to [1] or [2] above, wherein the multiple-effect distillation column comprises two distillation columns arranged in series.
[4] The method for producing an alcohol according to [1] or [2] above, wherein the multiple-effect distillation column comprises two distillation columns arranged in parallel.
[5] The method for producing an alcohol according to [1] or [2] above, wherein the multiple-effect distillation column comprises three distillation columns arranged in series.
[6] The producing method according to any one of [1] to [5] above, wherein the multiple-effect distillation column comprises at least a crude distillation column placed on the upstream side of the process, and a rectifying column placed on the downstream side of the process; and the concentration after concentration by the crude distillation column is from 40 to 60 wt %, and the concentration after concentration by the rectifying column is from 80 to 95 wt %.
[7] The producing method according to any one of [1] to [6] above, wherein the multiple-effect distillation column comprises at least a crude distillation column placed on the upstream side of the process, and a rectifying column placed on the downstream side of the process; and the reflux ratio of the crude distillation column is from 0 to 30, and the reflux ratio of the rectifying column is from 0.1 to 30.
[8] The method for producing an alcohol according to any one of [1] to [7] above, wherein the membrane separation apparatus comprises a porous support-zeolite membrane complex, in which a zeolite membrane is placed on a porous support.

[9] The method for producing an alcohol according to [8] above, wherein the molar ratio of $SiO_2/Al_2O_3$ in a zeolite composing the zeolite membrane is 5 or more.

[10] The method for producing an alcohol according to any one of [1] to [9] above, wherein the alcohol is ethanol.

[11] A system for producing an alcohol comprising a multiple-effect distillation column, a condenser for condensing a vapor recovered from the top of a distillation column, and a membrane separation apparatus for separating a water-alcohol mixed solution condensed in the condenser and introduced in a liquid phase.

According to the present invention, it is possible to provide a method for producing an alcohol utilizing a multiple-effect method achieving energy saving as a whole process.

DESCRIPTION OF THE EMBODIMENTS

Figure 1:
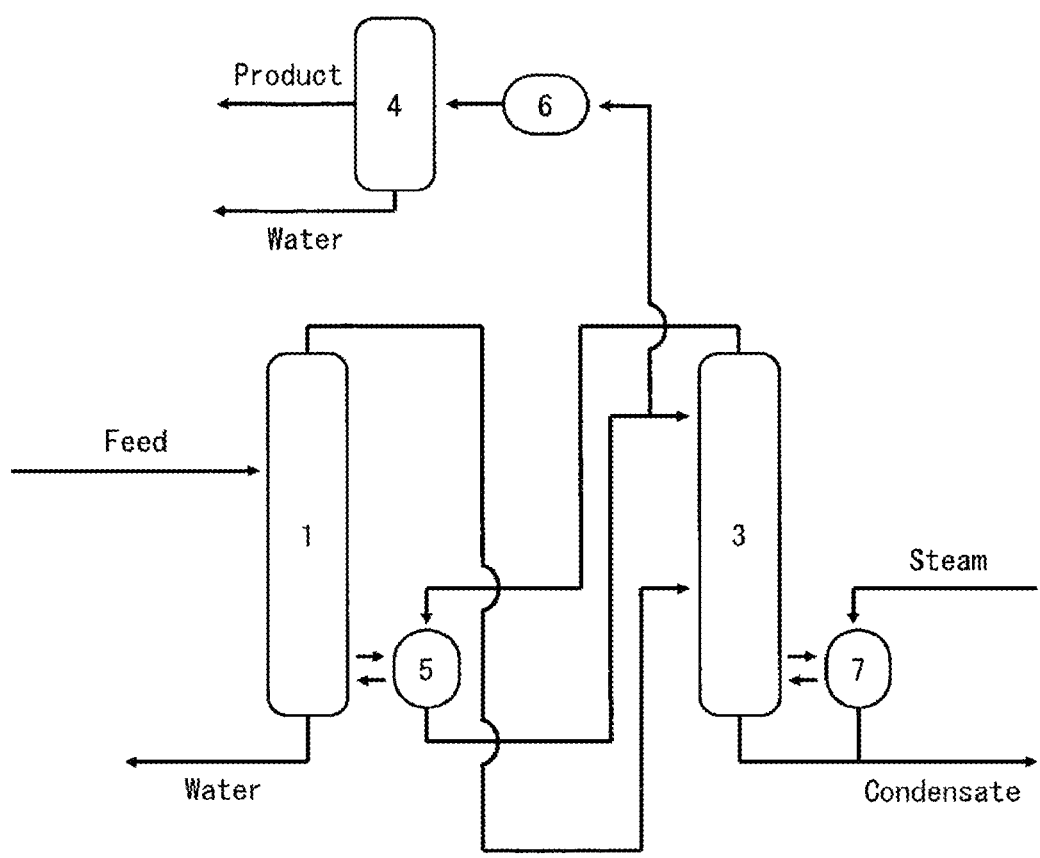
FIG. 1 is a flow diagram showing an embodiment of the present invention.

The present invention will be described in more detail, provided that the present invention be not limited only to the specific embodiment.

The method for producing an alcohol of an embodiment of the present invention includes a concentration step of introducing a water-alcohol mixed solution into a multiple-effect distillation column for concentrating the same; a condensation step of introducing a vapor recovered from the top of the distillation column into a condenser for condensing the same; and a separation step of introducing the water-alcohol mixed solution condensed in the condensation step in a liquid phase into a membrane separation apparatus for separating the water and alcohol in the mixed solution.

In this embodiment, a sufficient heat source of a distillation column is secured by condensing a water-alcohol mixed vapor recovered from the top of a distillation column, so that the energy efficiency is improved.

In the present embodiment, the concentration step is a step of increasing the alcohol concentration in the water-alcohol mixed solution, and the water-alcohol mixed solution is introduced into a multiple-effect distillation column to increase the alcohol concentration. As a heat source for distillation for the multiple-effect distillation column, in addition to a heat source such as a heater to be separately provided, the heat of condensation developed when a gas recovered from the top of a distillation column is condensed in a condenser is utilized.

As the multiple-effect distillation column usually one consisting of two or more distillation columns is used. As the number of the distillation columns performing heat exchange is increased, the amount of energy to be supplied from outside for evaporating a unit amount of water decreases. However, as the number of the distillation columns increases, the equipment cost increases. Therefore, the total number of distillation column is usually three or less. Considering equipment cost, energy efficiency, easiness of concentration operation, etc., usually a multiple-effect distillation column consisting of two to three distillation columns is used.

The multiple-effect distillation column may take a series arrangement, or a parallel arrangement. For example, two distillation columns are arranged in series, two distillation columns are arranged in parallel, or three distillation columns are arranged in series.

Each distillation column may be equipped with a side stripper.

When a side stripper is provided, the water-alcohol mixture can be withdrawn from one or several positions in the middle stage of a distillation column, and purified.

The above multiple-effect distillation column consists of two or more columns, and the distillation column placed most upstream of the process is herein referred to as a crude distillation column, and the distillation column placed most downstream of the process as a rectifying column.

The alcohol concentration of the distillate from the crude distillation column is usually 40 wt % or more, and may be 45 wt % or more in order to increase the energy efficiency of the whole process. Further, it is usually 60 wt % or less, and may be 55 wt % or less. Furthermore, the alcohol concentration of the distillate from the rectifying column is usually 80 wt % or more, and may be 82 wt % or more, or even 85 wt % or more in order to increase the energy efficiency of the whole process. Further, it is usually 95 wt % or less, and may be 94 wt % or less, or even 90 wt % or less.

When the alcohol concentration does not exceed the upper limit, there is a tendency that the load on the distillation column is reduced, and the energy efficiency of the whole process is enhanced. Further, when the alcohol concentration is not below the lower limit, the water concentration is not too high, and the filling amount of the adsorbent does not increase so much, and therefore a risk of increase in size of the adsorption equipment, or in equipment cost can be avoided. Therefore, the regeneration frequency of the adsorbent of the adsorption apparatus can be suppressed, and the operating cost also tends to be suppressed.

The water-alcohol mixed vapor recovered from the top of a distillation column that is a constituent of the multiple-effect distillation column is condensed by a condenser, and it is preferable that a portion of the condensate is returned to the gas phase in the distillation column, and the remaining condensate is withdrawn out of the distillation column. In this regard, the ratio of the flow rate of the condensate fed to the gas phase of the distillation column to the flow rate of the condensate withdrawn out of the distillation column (hereinafter referred to as "reflux ratio") is for the crude distillation column usually 0 or more, and may be 0.01 or more, 0.05 or more, 0.8 or more, or even 1.0 or more. Further, the reflux ratio is usually 30 or less, or may be 10 or less, 5.0 or less, 3.0 or less, 1.0 or less, or even 0.8 or less. For the rectifying column, the reflux ratio is usually 0.1 or more, or may be 0.2 or more, 0.5 or more, or even 1.0 or more. Further, it is usually 30 or less, or may be 10 or less, 5.0 or less, 3.0 or less, 1.0 or less, or even 0.8 or less.

When the reflux ratio is too high, the cost of the heat source for heating tends to increase, and the economic efficiency tends to decrease, and when the reflux ratio is too low, the reduction effect of solid matter precipitation within the distillation column cannot be obtained, and there is a tendency that mixing of a high boiling point component into the condensate increases due to deterioration of separation.

The temperature at the top of each column in the multiple-effect distillation column, including the crude distillation column and the rectifying column, is usually from 60 to 120° C. Therefore, although there is some heat loss, a low pressure steam in a temperature range of 80 to 110° C., or in terms of pressure in a range of 20 to 143 kPa can be generated utilizing the heat of condensation. Insofar as the temperature of the steam generated at the condenser is in the aforedescribed range, it can be favorable utilized in broader applications. For example, it can be supplied to a steam turbine to effectively recover the energy. A higher pressure level of the steam is more preferable, because the recoverable energy per unit mass is larger.

The operating pressure of each column in the multiple-effect distillation column, including the crude distillation column and the rectifying column, is preferably 0 kPa (absolute pressure) or more, especially preferably in a range of 0 to 350 kPa (absolute pressure). This is to increase the condensation efficiency by increasing the pressure of the mixed vapor of an alcohol and water supplied to a membrane separation apparatus. Although the condensation efficiency at a condenser is improved at a high pressure exceeding 350 kPa (absolute pressure), excessive pressure resistance of the distillation apparatus or the membrane separation apparatus is required and there may arise new problems such as an increase in apparatus size, and therefore such high pressure is not necessarily favorable.

The condensation step is a step of condensing the vapor of a water-alcohol mixed solution recovered from the top of each of the distillation columns, where the vapor of a water-alcohol mixed solution is fed into a condenser and condensed. In the condensation step, the condensation ratio with respect to the total vapor fed into the condenser in terms of weight is usually 30% or more, preferably 50% or more, more preferably 90% or more, and especially preferably 99% or more from the viewpoint of improving the overall energy efficiency. When the condensation ratio with respect to the total vapor fed into the condenser is 99% or more, such condensation is herein referred to as "total condensation".

When, for example, a kettle type heat exchanger, or a thin film evaporator is used as a condenser, low pressure steam, for example 0.07 atm (absolute pressure) steam (90° C.) can be generated utilizing the heat of condensation developed in condensing the column overhead vapor. In this way, the heat of condensation can be utilized effectively, which is preferable from the viewpoint of energy efficiency. In this regard, the low-pressure steam means low-pressure steam which is generated when water functioning as a coolant in the condenser is heated by means of heat exchange in the condenser.

In the present embodiment for the separation step, a pervaporation (PV) method of feeding the mixed solution in a liquid phase to the membrane separation apparatus is adopted.

Conventionally, as a separation membrane for a membrane separation apparatus used together with a multiple-effect distillation column, a polymer membrane or the like inferior in durability was used. Namely, deterioration of the membrane due to contact with the liquid phase was significant, and therefore vapor feed, or feed in a gas phase to the membrane separation apparatus was necessary. As a result, the vapor recovered from the top after the concentration step could be condensed only to a limited portion, and therefore only partial heat utilization was possible.

Since liquid feed in a liquid phase to the membrane separation apparatus is possible in the present embodiment, condensation with high efficiency is possible, and a large portion of the heat of condensation can be utilized. Therefore, it is possible to improve the energy efficiency as a whole process.

In a PV method, water permeation is performed by bringing a liquid of a water-containing organic compound, such as a water-containing organic acid, a water-containing alcohol, and a water-containing organic solvent, into contact with a separation membrane of a membrane separation apparatus. That is, this system is also called permeation vaporization or penetrative vaporization, and the liquid of a water-containing organic compound (feed liquid) is evaporated intercalating a separation membrane, through which only water is allowed to pass the membrane so that an organic compound, such as an organic acid, an alcohol, and an organic solvent, is separated and concentrated. Since the feed liquid is cooled by the heat of vaporization, a heating means is needed to compensate for it.

The temperature of the water-alcohol mixture in a liquid phase fed to a membrane separation apparatus is usually from 25 to 200° C., and preferably from 70 to 150° C. The operating pressure is usually from 0.1 to 1.5 MPa, and preferably from 0.2 to 0.8 MPa.

Although the PV method employs a circulation system, it may also adopt a non-circulation system. Further, for driving the apparatus, a sweep gas system, in which nitrogen, dry air or the like is supplied to a permeation chamber, may be adopted in place of the vacuum system. The number of columns installed in the apparatus may be appropriately selected according to the conditions, and it may be one, or two or more. Further, before an alcoholic beverage is fed to the apparatus, a filter may be installed for removing a solid matter in the alcoholic beverage.

The alcohol concentration of a water-alcohol mixed solution fed to a membrane separation apparatus is from 75 to 99 wt %, preferably from 76 to 98 wt %, more preferably from 77 to 97 wt %, further preferably further from 78 to 96 wt %, especially preferably from 79 to 95 wt %, and most preferably from 80 to 94 wt %. When the same is concentrated only less than 75 wt %, the load to the membrane separation apparatus becomes too heavy, and the size requirement of the membrane separation apparatus becomes too large. Therefore, it is not preferable, because it is not any more possible to yield an anhydrous alcohol by purifying the water-alcohol mixed solution more simply and extremely energy efficiently as the whole process. Meanwhile, when the same is concentrated beyond 99 mass %, it becomes also impossible to yield an anhydrous alcohol by purifying the water-alcohol mixed solution more simply and extremely energy efficiently as the whole process.

An alcohol yielded after introduction to a membrane separation apparatus in the separation step can be used as a product when its concentration is sufficiently high. When the concentration is not high enough, it can be returned to the adsorption step, or the separation step.

Meanwhile, the permeation flux of water in a membrane separation apparatus is preferably 0.1 kg/(m$^2$·h) or more, more preferably 2.0 kg/(m$^2$·h) or more, and further preferably 5.0 kg/(m$^2$·h) or more. When the permeation flux of water is in the aforedescribed range, in a case where the product is obtained directly from the membrane separation apparatus, the production efficiency can be enhanced, and in a case where the permeate is sent back from the membrane separation apparatus to the adsorption apparatus, the energy efficiency of the adsorption apparatus can be enhanced. Further, when the value of the permeation flux is large, it is possible to design a smaller separation membrane area, and to downsize the apparatus, while keeping the desired concentration amount and concentration rate in the membrane separation apparatus There is no particular restriction on a membrane separation apparatus, insofar as it has a separation membrane, which is usually a separation membrane having a dehydration function. Examples thereof include a dialysis membrane, a microfiltration membrane (MF membrane), an ultrafiltration membrane (UF membrane), a nanofiltration membrane (NF membrane), a reverse osmosis membrane (RO membrane), a zeolite membrane, and a mixed matrix membrane, in which zeolite or the like is added to a polymer membrane (hereinafter also referred to as "MMM"). There is also no particular restriction on the shape thereof, and it may be any of flat, tubular, honeycomb, monolithic, and hollow fiber shapes. From the viewpoint of separation performance, it is preferable to use a nanofiltration membrane, a reverse osmosis membrane, a zeolite membrane, or an MMM, and from the point of durability it is preferable to use a zeolite membrane.

As an example of a separation membrane, a zeolite membrane will be described in detail below.

As a zeolite membrane, it is preferable to use a porous support-zeolite membrane complex (hereinafter also referred to as "zeolite membrane complex") in which a zeolite membrane is placed on a porous support.

There is no particular restriction on the porous support, insofar as it has such a chemical stability so that it can tightly adsorb, or preferably crystalize, zeolite in a film form on the surface, and is porous. Among others, an inorganic porous support is preferable, and examples thereof include sintered ceramics, such as silica, α-alumina, γ-alumina, mullite, zirconia, titania, yttria, silicon nitride, and silicon carbide, sinteredmetals, such as iron, bronze, and stainless steel, glass, and molded carbon.

Among inorganic porous supports, a porous support containing a sintered body of a ceramic, the basic part or most part of which is a solid material composed of an inorganic non-metallic substance (ceramics support) is especially preferable, because the adhesion at the interface is strengthened by zeolitization of a part of the support during synthesis of a zeolite membrane.

Specific examples thereof include sintered ceramics (ceramic supports) containing silica, α-alumina, γ-alumina, mullite, zirconia, titania, yttria, silicon nitride, and silicon carbide, or the like. Among them, a porous support containing at least one of alumina, silica, and mullite is preferable, because zeolitization of a part of the porous support is easy so that the bond between the porous support and zeolitize becomes firm and a dense membrane with a high separation performance can be easily formed.

Since a zeolite membrane complex has a support, its mechanical strength is increased so that handling becomes easier allowing flexible design of a variety of apparatus. In particular, in a case where an inorganic porous support is used as a support (inorganic porous support-zeolite membrane complex), since it is composed of an inorganic substance, it is superior in heat resistance and chemical resistance.

There is no particular restriction on the shape of a porous support, insofar as a mixture of liquid or gas can be effectively separated. Specific examples thereof include a flat shape, a tubular shape, a honeycomb shape with a large number of cylindrical, columnar, or prismatic pores, and a monolithic shape, and any of these shapes may be used.

It is preferable that zeolite is crystallized on the surface of a porous support (hereinafter also referred to as "porous support surface").

Although there is no particular restriction on the average pore size at the porous support surface, it is preferable that the pore size is regulated usually at 0.02 μm or more, preferably 0.05 μm or more, further preferably 0.1 μm or more, and especially preferably 0.5 μm or more, and usually at 20 μm or less, preferably 10 μm or less, and more preferably 5 μm or less.

When the average pore size is too small, the permeated amount tends to decrease, and when it is too large, the strength of a support itself may become insufficient, and the percentage of pores in the support surface increases and a dense zeolite membrane may be hardly formed.

The average thickness of a porous support is usually 0.1 mm or more, preferably 0.3 mm or more, more preferably 0.5 mm or more, and especially preferably 0.7 mm or more; and usually 7 mm or less, preferably 5 mm or less, and more preferably 3 mm or less.

The support is used for endowing a zeolite membrane with favorable mechanical strength. Therefore, when the average thickness is too thin, a porous support-zeolite membrane complex cannot be strong enough, and the porous support-zeolite membrane complex is vulnerable to shocks or vibrations, which tends to cause problems in a practical use. When the average thickness of a support is too thick, the diffusion of a permeated substance tends to be poor, and the permeation flux tends to decrease.

When the porous support is a cylindrical tube, the outer diameter of the cylindrical tube is usually 3 mm or more, preferably 5.5 mm or more, more preferably 9.5 mm or more, and especially preferably 11 mm or more, and usually 51 mm or less, preferably 31 mm or less, more preferably 21 mm or less, further preferably 17 mm or less, and especially preferably 15 mm or less.

Although the support is used for endowing a zeolite membrane with favorable mechanical strength, in a case where the support is a cylindrical tube, when the outer diameter is too small, a porous support-zeolite membrane complex cannot be strong enough, and the porous support-zeolite membrane complex is vulnerable to shocks or vibrations, which tends to cause problems in a practical use. In a case where the support is a cylindrical tube, when the outer diameter is too large, the membrane area per volume decreases, and therefore the volume of membrane required for obtaining a necessary membrane area becomes so large, that a large installation space, or a large sized module tends to be required, which is economically disadvantageous.

Further, the surface of a porous support is preferably smooth, and the surface may be polished according to need with a file, or the like.

Incidentally, a porous support surface means, for example, a surface portion of an inorganic porous support, on which zeolite is crystallized. The surface may be any part of surface, or surfaces, irrespective of the respective shapes. For example, in the case of a support in a cylindrical tube form it may be the outer surface, or the inner surface, or both the outer surface and the inner surface, as the case may be.

Further, there is no particular restriction on the pore size of the porous support at a portion other than the porous support surface.

The porosity of the porous support is usually 20% or more, preferably 25% or more, and more preferably 30% or more, and usually 70% or less, preferably 60% or less, and more preferably 50% or less.

The porosity of the porous support has a strong influence on the permeation flow rate at the time of separation of a gas or a liquid. When the porosity is less than the aforedescribed lower limit, the diffusion of a permeated substance tends to be impeded, and when the porosity exceeds the aforedescribed upper limit, the strength of the porous support tends to be decreased.

The molar ratio $SiO_2/Al_2O_3$ of a zeolite constituting a zeolite membrane is preferably 5 or more, more preferably 8 or more, further preferably 10 or more, and especially preferably 12 or more, and usually 2000 or less, preferably 1000 or less, more preferably 500 or less, further preferably 100 or less, especially preferably 20 or less, and most preferably 17 or less. When the molar ratio $SiO_2/Al_2O_3$ is less than the lower limit, the durability tends to decrease, and when it exceeds the upper limit, the hydrophobicity is too strong, so the permeation flux tends to decrease.

The molar ratio of $SiO_2/Al_2O_3$ in the present invention is a value determined by a scanning electron microscope—energy dispersive X-ray spectrometry method (SEM-EDX). In order to obtain information solely on a few micron-thick membrane, a measurement is performed usually with an X-ray at the accelerating voltage of 10 kV.

Although there is no particular restriction on the framework density of a main zeolite constituting a zeolite membrane, it is preferably 10.0 T/1000 Å$^3$ or more, and more preferably 14.0 T/1000 Å$^3$ or more, and preferably 18.0 T/1000 Å$^3$ or less, more preferably 17.0 T/1000 Å$^3$ or less, further preferably 16.0 T/1000 Å$^3$ or less, and most preferably 15.0 T/1000 Å$^3$ or less. The aforedescribed range is preferable from the viewpoint of durability.

A framework density means the number of T elements constituting the framework of a zeolite other than oxygen per 1000 Å$^3$ of the zeolite, and this value is determined by the structure of the zeolite. The relationship between the framework density and the structure of a zeolite is shown in ATLAS OF ZEOLITE FRAMEWORK TYPES, Fifth Revised Edition 2001 ELSEVIER.

A main zeolite constituting a zeolite membrane is usually a zeolite having a 6 to 12-membered oxygen ring structure, preferably a 6 to 10-membered oxygen ring structure, and more preferably an 8-membered oxygen ring.

In this case, the value n of a zeolite having an n-membered oxygen ring indicates the largest oxygen number among pores constituted with oxygen and T elements forming the zeolite framework. For example, when there are a pore with a 12-membered oxygen ring and a pore with an 8-membered oxygen ring as in a MOR type zeolite, it is regarded as a zeolite of a 12-membered oxygen ring.

Examples of a zeolite having an 6 to 10-membered oxygen ring structure include AEI, AEL, AFG, ANA, BRE, CAS, CDO, CHA, DAC, DDR, DOH, EAB, EPI, ESV, EUO, FAR, FRA, FER, GIS, GIU, GOO, HEU, IMF, ITE, ITH, KFI, LEV, LIO, LOS, LTA, LTN, MAR, MEP, MER, MEL, MFI, MFS, MON, MSO, MTF, MTN, MTT, MWW, NAT, NES, NON, PAU, PHI, RHO, RRO, RTE, RTH, RUT, SGT, SOD, STF, STI, STT, TER, TOL, TON, TSC, TUN, UFI, VNI, VSV, WEI, and YUG.

When the structure is larger than a 10-membered oxygen ring structure, the pore size becomes large, and for an organic substance having a small size, the separation performance is decreased, and the application thereof may be limited.

Among the above, preferable zeolite structures are AEI, CHA, KFI, LEV, LTA, PAU, RHO, RTH, and UFI; more preferable are CHA, LEV, LTA, and UFI; further preferable are CHA or LTA; and especially preferable is LTA.

Although there is no particular restriction on the thickness of a zeolite membrane, it is usually 0.1 μm or more, preferably 0.6 μm or more, more preferably 1.0 μm or more, further preferably 5 μm, and especially preferably 7 μm or more. Further, it is usually in a range of 100 μm or less, preferably 60 μm or less, more preferably 20 μm or less, and especially preferably 10 μm or less. When the membrane thickness is too large, the permeated amount tends to decrease, and when it is too small, the selectivity or the membrane strength tends to decrease.

Although there is no particular restriction on the particle diameter of a zeolite that forms a zeolite membrane, when it is too small, there is a tendency that the grain boundary becomes large to decrease the permeation selectivity, etc. Therefore, the diameter is usually 30 nm or more, preferably 50 nm or more, and more preferably 100 nm or more, and the upper limit is the membrane thickness or less. More preferably, the particle diameter of zeolite is the same as the membrane thickness. This is because, when the particle size of a zeolite is the same as the membrane thickness, the grain boundary of the zeolite becomes minimum. A zeolite membrane obtained by hydrothermal synthesis is preferable, because the particle diameter of the zeolite may become the same as the membrane thickness.

A zeolite membrane may be produced by a heretofore well-known hydrothermal synthesis method, or the like, and the zeolite membrane may be optionally subjected to a silylation treatment using a silylation agent.

The alcohol concentration in water from which an alcohol is removed by a membrane separation apparatus is usually less than 10 mass %, preferably less than 5 mass %, more preferably less than 1 mass %, further preferably less than 0.8 mass %, especially preferably less than 0.5 mass %, and most preferably less than 0.3 mass %.

A separation operation with an alcohol-selective separation membrane may be repeated, and an alcohol containing solution having permeated a separation membrane may be separated again with an alcohol-selective separation membrane to remove the alcohol down to a desired alcohol concentration. Further, an alcohol containing solution having permeated a separation membrane may be fed again to the separation step.

There is no particular restriction on an alcohol in a water-alcohol mixed solution in the present embodiment, and examples thereof may ordinarily include methanol, ethanol, n-propanol, isopropanol, n-butanol, isobutanol, t-butanol, and n-octanol, and for example ethanol is preferable.

In the present embodiment, a step other than the concentration step, the condensation step, and the separation step may be also included. For example, before the concentration step, a fermentation step may be employed for fermenting an alcohol fermentation raw material to yield a water-alcohol mixture.

Furthermore, in the present embodiment, a pulverizing step may be employed for pulverizing an alcohol fermentation raw material for facilitating fermentation.

As a raw material, a cellulose-containing raw material is used, and examples thereof include a saccharine material, such as sugarcane and sugar beet; a tuber, such as sweet potato and potato; a starch-rich raw material, such as grains including corn, barley, and rice; and a fiber-rich raw material, such as wastepaper and waste lumber.

Further, in the present embodiment, when the alcohol concentration of a water-alcohol mixed solution supplied to the crude distillation column placed on the upstream side of the concentration step is low, the water-alcohol mixed solution may be fed before the concentration step to a preliminary distillation column such as a moromi column to increase the alcohol concentration. From the viewpoint of reducing energy consumption, it is preferable to increase the alcohol concentration in the preliminary distillation column usually to 30 mass % or more, preferably 35 mass % or more, more preferably 40 mass % or more, and further preferably 45 mass % or more. Although there is no particular restriction on the upper limit, it is usually less than 70 mass %, preferably 65 mass % or less, more preferably 60 mass % or less, and further preferably 55 mass % or less. When the alcohol concentration is in the above range, almost no reflux is required, and the amount of water to be evaporated is also small.

Also, if necessary, filtration, such as microfiltration, ultrafiltration, and nanofiltration, or a neutralization treatment may be performed singly or in a combination in order to remove an unnecessary substance, or a high molecular weight component in the solution.

An alcohol production system of another embodiment of the present invention is an alcohol production system that includes at least a multiple-effect distillation column, a condenser for condensing a vapor recovered from the top of the distillation column, and a membrane separation apparatus for separating a water-alcohol mixed solution condensed in the condenser and fed in a liquid phase.

Specific embodiments will be described below with reference to drawings, provided that the present invention be not limited to the specific embodiments described below.

FIG. 1 shows a process flow regarding a method for producing an alcohol in the case of using a multiple-effect distillation column constituted with two distillation columns arranged in series. In FIG. 1, the column positioning on the upstream side of the process is a crude distillation column 1, and the column positioning on the downstream side of the process is a rectifying column 3.

The liquid charged into the process flow is a water-alcohol mixed solution, and is fed into the crude distillation column 1 and concentrated, and is sent to the rectifying column 3 and further concentrated. The water-alcohol mixed vapor recovered from the top of the rectifying column 3 is fed to a condenser 5 and condensed. A portion of the condensed water-alcohol mixed solution is fed to a membrane separation apparatus 4, and excluding such portion the remaining water-alcohol mixed solution is refluxed to the rectifying column 3. The water-alcohol mixed solution fed to the membrane separation apparatus 4 is further concentrated in terms of the alcohol concentration, and a high concentration alcohol is supplied as a product.

The heat of condensation developed at the time of condensation in the condensers 5, and 7 as well as a condenser 6, which is however not illustrated, is utilized as distillation heat sources for the crude distillation column 1, and the rectifying column 3, respectively, to enhance the energy efficiency of the whole process.

The wastewater discharged from the distillation column 1 and the membrane separation apparatus 4 is separated and removed, or may be fed to, for example, a multiple-effect distillation column, a fermenting vessel, or a moromi column (not illustrated).

Figure 2:
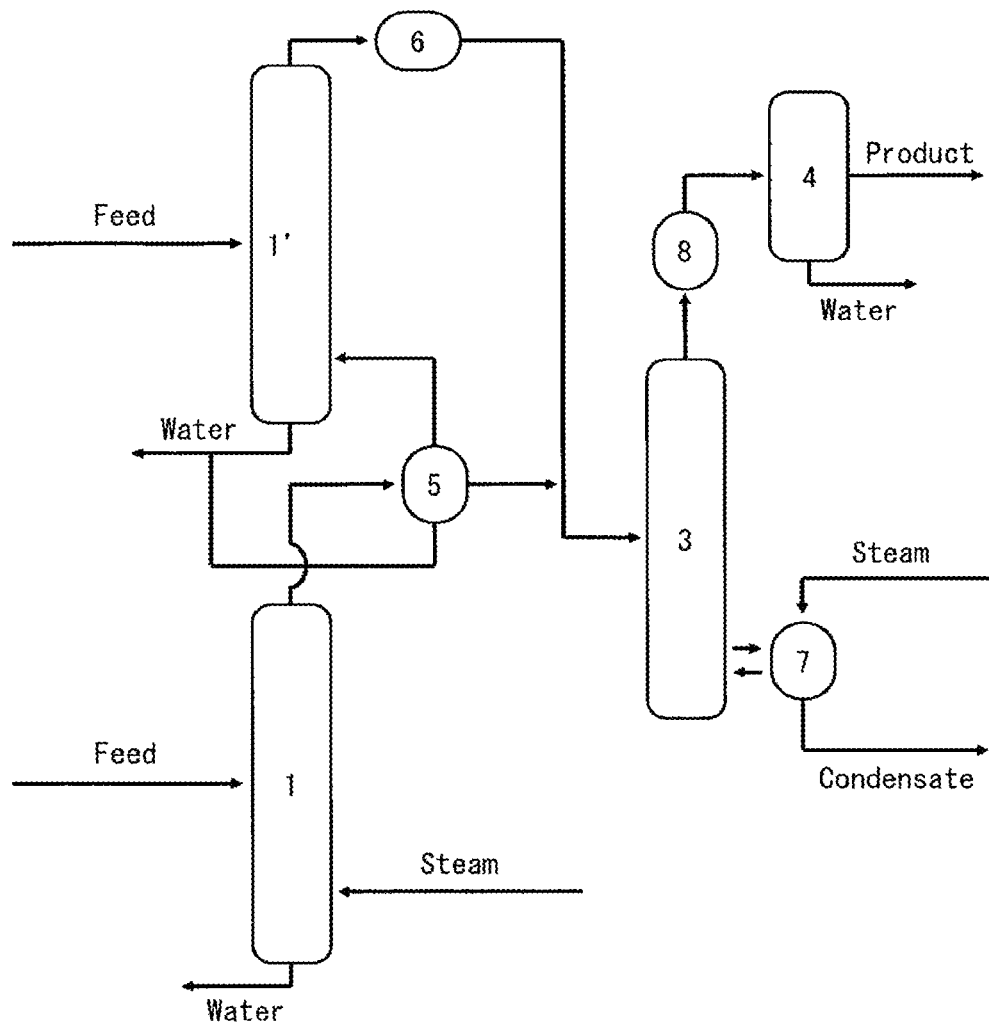
FIG. 2 is a flow diagram showing an embodiment of the present invention.

FIG. 2 shows a process flow regarding a method for producing an alcohol in the case of using a multiple-effect distillation column constituted with three distillation columns, two of which positioning on the upstream side are arranged in parallel. In FIG. 2, the two columns positioning on the upstream side of the process are crude distillation columns 1, and 1', and the column positioning on the downstream side of the process is a rectifying column 3.

The liquid charged into the process flow is a water-alcohol mixed solution, and is fed to each of the crude distillation columns 1 and 1' and concentrated. The water-alcohol mixed vapor recovered from the top of the crude distillation column 1 is fed to a condenser 5 and condensed. The condensation at the condenser 5 is preferably total condensation. A portion of this condensed water-alcohol mixed solution is fed to the crude distillation column 1', a portion is fed to the rectifying column 3, and the rest is removed as wastewater. The water-alcohol mixed vapor recovered from the top of the crude distillation column 1' is fed to a condenser 6 and condensed, and fed to the rectifying column 3 and further concentrated. The water-alcohol mixed vapor recovered from the top of the rectifying column 3 is fed to a condenser 8 and condensed. The condensed water-alcohol mixed solution is fed to a membrane separation apparatus 4 to further increase the alcohol concentration. The high concentration alcohol is supplied as a product.

The heat of condensation developed at the time of condensation in a condenser 7 and a condenser 8, which is however not illustrated, is utilized as a distillation heat source for the rectifying column 3 to enhance the energy efficiency of the whole process.

The wastewater discharged from the crude distillation columns 1 and 1', the condenser 5, and the membrane separation apparatus 4 is separated and removed, or may be fed to, for example, another distillation column, a fermenting vessel, or a moromi column (not illustrated).

Figure 3:
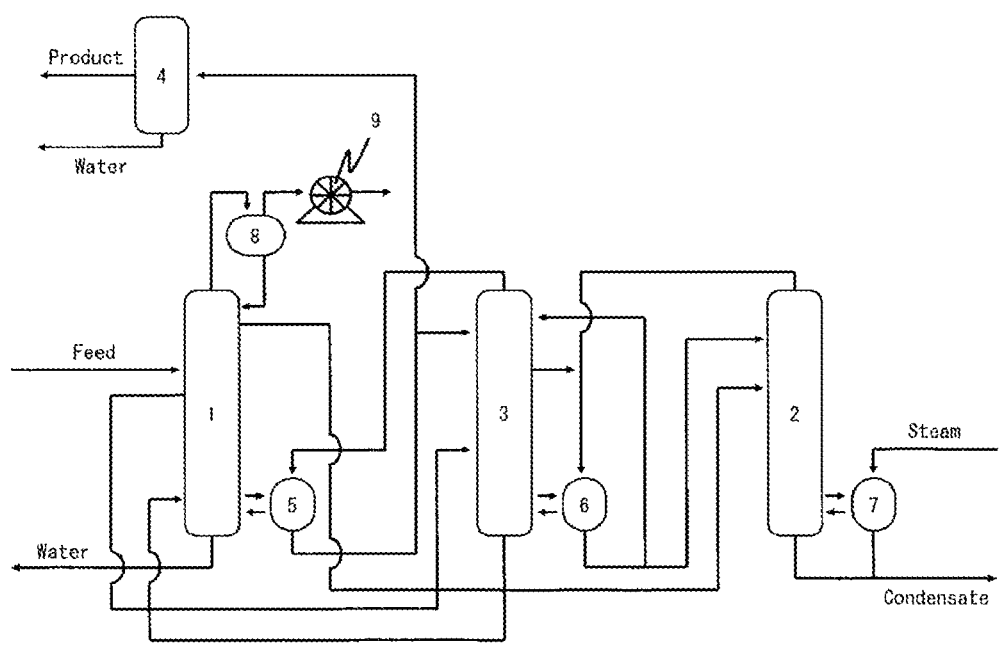
FIG. 3 is a flow diagram showing an embodiment of the present invention.

FIG. 3 shows a process flow regarding a method for producing an alcohol in the case of using a multiple-effect distillation column constituted with three distillation columns arranged in series In FIG. 3, the column positioning on the upstream side of the process is a crude distillation column 1, and the column positioning on the downstream side of the process is a rectifying column 3.

The liquid charged into the process flow is a water-alcohol mixed solution, and is fed to the crude distillation column 1 and concentrated. The water-alcohol solution distilled out from the top of the crude distillation column 1 is fed to the distillation column 2 and further concentrated, and sent to a condenser 6 and condensed. A portion of the condensed water-alcohol mixed solution is fed to the rectifying column 3, and excluding such portion the remaining water-alcohol mixed solution is refluxed to the distillation column 2. The water-alcohol mixed solution fed to the rectifying column 3 is further concentrated, and fed to a condenser 5 and condensed. A portion of the condensed water-alcohol mixed solution is fed to the membrane separation apparatus 4, and excluding such portion the remaining water-alcohol mixed solution is refluxed to the rectifying column 3. The water-alcohol mixed solution fed to the membrane separation apparatus 4 is further concentrated in terms of the alcohol concentration in the membrane separation apparatus 4, and a high concentration alcohol is supplied as a product.

The water-alcohol mixed vapor recovered from the top of the crude distillation column 1 is fed to a condenser 8 and condensed. A portion of the condensed water-alcohol mixed solution is fed to a vacuum pump 9, and excluding such portion the remaining water-alcohol mixed solution is refluxed to the crude distillation column 1.

The heat of condensation developed at the time of condensation in the condensers 5, 6, and 7 is utilized as distillation heat sources for the crude distillation column 1, the rectifying column 3, and the distillation column 2 respectively, to enhance the energy efficiency of the whole process.

The wastewater discharged from the crude distillation column 1 and the membrane separation apparatus 4 is separated and removed, or may be fed to, for example, another distillation column, a fermenting vessel, or a moromi column (not illustrated).

Although the present invention has been described with reference to specific embodiments, each embodiment was presented as an example and does not limit the scope of the present invention. Each of the embodiments described herein can be variously modified without departing from the spirit of the invention, and can be combined with characteristics described by other embodiments so long as it can be enabled.

REFERENCE SIGNS LIST 1, 1' Crude distillation column
2 Distillation column
3 Rectifying column
4 Membrane separation apparatus
5 Condenser
6 Condenser
7 Condenser
8 Condenser
9 Vacuum pump

What is claimed is:

1. A method for producing an alcohol comprising:
   a concentration step of introducing a water-alcohol mixed solution into a multiple-effect distillation column to concentrate the water-alcohol mixed solution;
   a condensation step of introducing a vapor recovered from the top of the multiple-effect distillation column into a condenser to condense the vapor totally, and
   a separation step of introducing the water-alcohol mixed solution condensed in the condensation step in a liquid phase into a membrane separation apparatus to separate the water and alcohol in the mixed solution,
   wherein the heat of condensation developed when the vapor recovered from the top of the distillation column is condensed in a condenser is utilized as a heat source for the concentration step.

2. The method for producing an alcohol according to claim wherein the multiple-effect distillation column comprises two distillation columns arranged in series.

3. The method for producing an alcohol according to claim 1, wherein the multiple-effect distillation column comprises two distillation columns arranged in parallel.

4. The method for producing an alcohol according to claim 1, wherein the multiple-effect distillation column comprises three distillation columns arranged in series.

5. The method for producing an alcohol according to claim 1, wherein the multiple-effect distillation column comprises at least a crude distillation column placed on the upstream side of the process, and a rectifying column placed on the downstream side of the process; and the alcohol concentration of the distillate after concentration by the crude distillation column is from 40 to 60 wt %, and the alcohol concentration of the distillate after concentration by die rectifying column is from 80 to 95 wt %.

6. The method for producing an alcohol according to claim 1, wherein the multiple-effect distillation column comprises at least a crude distillation column placed on the upstream side of the process, and a rectifying column placed on the downstream side of the process; and the reflux ratio of the crude distillation column is from 0 to 30, and the reflux ratio of the rectifying column is from 0.1 to 30.

7. The method for producing an alcohol according to claim 1, wherein the membrane separation apparatus comprises a porous support-zeolite membrane complex, in which a zeolite membrane is placed on a porous support.

8. The method for producing an alcohol according to claim 7, wherein the molar ratio of $SiO_2/Al_2O_3$ in a zeolite composing the zeolite membrane is 5 or more.

9. The method for producing an alcohol according to claim 8, wherein the zeolite has an LTA structure.

10. The method for producing an alcohol according to claim 8, Wherein a thickness of the zeolite membrane is in a range from 0.1 to 100 μm, and
    wherein the zeolite is in the form of particles having a diameter equal to the thickness of the zeolite membrane.

11. The method for producing an alcohol according to claim 10, wherein a thickness of the zeolite membrane is in a range from 0.1 to 10 μm.

12. The method for producing an alcohol according to claim 1, wherein the alcohol is ethanol.

13. The method for producing an alcohol according to claim 1, wherein the condensation ratio with respect to the total vapor fed into the condenser in terms of weight is 99% or more.

14. The method for producing an alcohol according to claim 1, wherein the beat of condensation is utilized to generate low-pressure steam to provide the heat source.

* * * * *